United States Patent [19]

Lutgendorf et al.

[11] Patent Number: 4,680,463
[45] Date of Patent: Jul. 14, 1987

[54] APPARATUS FOR CHECKING CONTAINERS

[75] Inventors: Pieter H. Lutgendorf, Deventer; Gerrit J. Kleinnibbelink, Ugchelen, both of Netherlands

[73] Assignee: Hajime Industries Ltd., Tokyo, Japan

[21] Appl. No.: 599,696

[22] Filed: Apr. 12, 1984

[30] Foreign Application Priority Data

Apr. 22, 1983 [NL] Netherlands ............... 8301420
Aug. 29, 1983 [NL] Netherlands ............... 8303007

[51] Int. Cl.$^4$ ............................................. G01N 9/04
[52] U.S. Cl. ........................... 250/223 B; 356/240
[58] Field of Search ............. 250/223 R, 223 B, 224, 250/572; 356/240

[56] References Cited

U.S. PATENT DOCUMENTS 3,886,353  5/1975  Shioya ..................... 250/223 B

Primary Examiner—Gene Wan
Attorney, Agent, or Firm—John P. Snyder

[57] ABSTRACT

The invention relates to an apparatus for checking containers, e.g. bottles or pots by means of a transport apparatus for transporting the containers along a predetermined path and a lighting apparatus positioned at a side of said path, e.g. at least one flash light means, and a sensing apparatus, e.g. at least one video camera positioned on a corresponding position, said transport apparatus being provided, in the area of said lighting apparatus and said sensing apparatus a part, in which the containers are hung by their collars. The invention proposes to adapt an apparatus of the type mentioned in the preamble in such a way that in said part of said transport apparatus the path is rectilinear, thus avoiding the need of using means to counteract the oblique position necessary in prior art apparatus, in which the path is curved, and avoiding mechanical load due to centrifugal forces.

14 Claims, 4 Drawing Figures

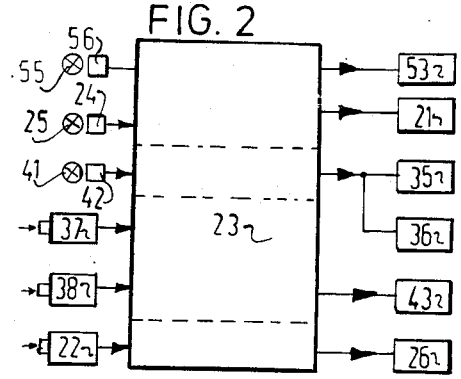
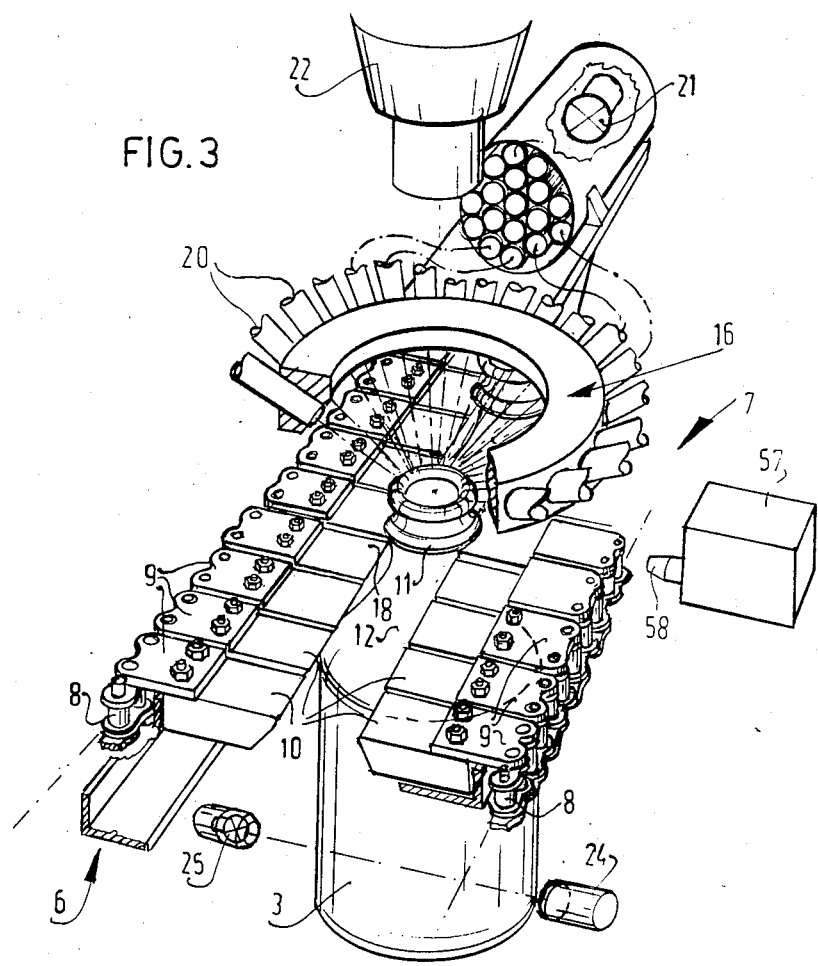

APPARATUS FOR CHECKING CONTAINERS

The invention relates to an apparatus for checking containers, e.g. bottles or pots by means of a transport apparatus for transporting the containers along a predetermined path and a lighting apparatus positioned at a side of said path, e.g. at least one flash light means, and a sensing apparatus, e.g. at least one video camera positioned on a corresponding position, said transport apparatus being provided, in the area of said lighting apparatus and said sensing apparatus a part, in which the containers are hung by their collars.

In the manufacturing of such containers or at least prior to filling them with e.g. beverages, it is necessary to verify whether the containers satisfy certain quality criteria. E.g. it has to be possible to assess if a container exhibits a crack that during transport of after bringing a container under an overpressure or underpressure may give raise to breaking or even exploding the container. Further it is necessary to verify if at the inner surface of the container, there are irregularities in the surface, or in case of re-use of containers dirt or the like which deteriorate in an intolerable manner the contents of the container and/or affect the presentation and visual attractivity. E.g. for use of crown caps it is important that the upper edge of each container exhibits a desired regular shape and a smooth sealing surface. This circumstance is further important in connection with the fact that users often bring containers directly to their mouths for drinking; in this connection a sharp edge may be dangerous.

An apparatus of the type described above is known from DE-A-27 17 955. The apparatus known herefrom comprises a transport apparatus for the partially hanging transport of the containers over a curved path. The supplying of the containers takes place by means of a transport conveyor. Supply into the apparatus takes place by means of a worm wheel pushing the containers into a star wheel. It will be clear that the worm wheel and this star wheel have to be synchronized. Even in case of a perfect synchronization in practice it appears that such apparatus have a high sensitivity to defects. E.g. the star wheel is propense to jamming, e.g. by lack of steadiness of sizes of glass containers, differences in sizes, particularly in case of the market of return bottles and mutual shape deviations due to which pinching may occur. In practice jammed bottles are broken into pieces by means of a hammer. Particularly at higher speeds the chance of faults is higher. The remedy of faults may be very time consuming and therefore costly.

A further disadvantage of the prior art apparatus is residing in the fact that the worm wheel rubs along the outer surface of the containers to be transported, causing damages and producing noise.

The transportation through a curved path always causes the occurrence of centrifugal forces by which the transported containers are apt to an oblique hanging position. Therefore means are necessary to counteract this oblique position, particularly in the case in which the containers have to be checked in that path. Further generally centrifugal forces cause mechanical loads.

For modification of the apparatus for another type of containers, in particular another diameter another worm wheel and another star wheel is necessary, whilst also the synchronization has to be adapted. Such a new adjustment takes a long time in the order of magnitude of an hour.

It is the purpose of the invention to solve the limitations and disadvantages of the prior art. In particular it is the aim of the invention to enhance the possible transport speed, to decrease the production costs of a checking apparatus to minimize the space occupation, to make a simpler adaptation to other types of containers possible and to assure a minimum mechanical load.

In view of the above objects the invention proposes to adapt an apparatus of the type mentioned in the preamble in such a way that in said part of said transport apparatus the path is rectilinear.

In a variant the apparatus may be characterized in that for checking the collar of each container the containers are guided along a circle of light conductors connected with a flash light means, that the axis of said circle coincides with the optical axis of the sensing apparatus and that the flash light means is adapted to supply a flash on the moment at which the optical axis and the axis of the collar coincide.

In a further variant the apparatus may be characterized in that for checking the bottom of each container the containers are guided along a flash light means co-operating with a video camera, said video camera and said flash light means having a substantially vertical optical axis in common, that the flash light means is adapted to supply a flash on the moment, on which a container passes said optical axis with the axis of its collar and that said video camera is positioned at the one side of the bottom and the flash light means at the other side of said bottom.

For checking the bottoms of transparent bottles such an apparatus may be characterized in that the flash light means is positioned under the bottom and the video camera is positioned above the neck of the bottles passing.

BRIEF DESCRIPTION OF THE DRAWING FIGURES

The invention will now be explained with reference to the drawing. In the drawing show:

FIG. 1 a perspective view of a checking apparatus according to the invention.

FIG. 2 a block diagram of a control apparatus forming part of the checking apparatus according to FIG. 1;

FIG. 3 a perspective view partially broken away of a detail of the checking apparatus according to FIG. 1; and FIG. 4 a schematic perspective view partially broken away of a part of a variant of the apparatus according to the invention.

DETAILED DESCRIPTION

Figure 1:
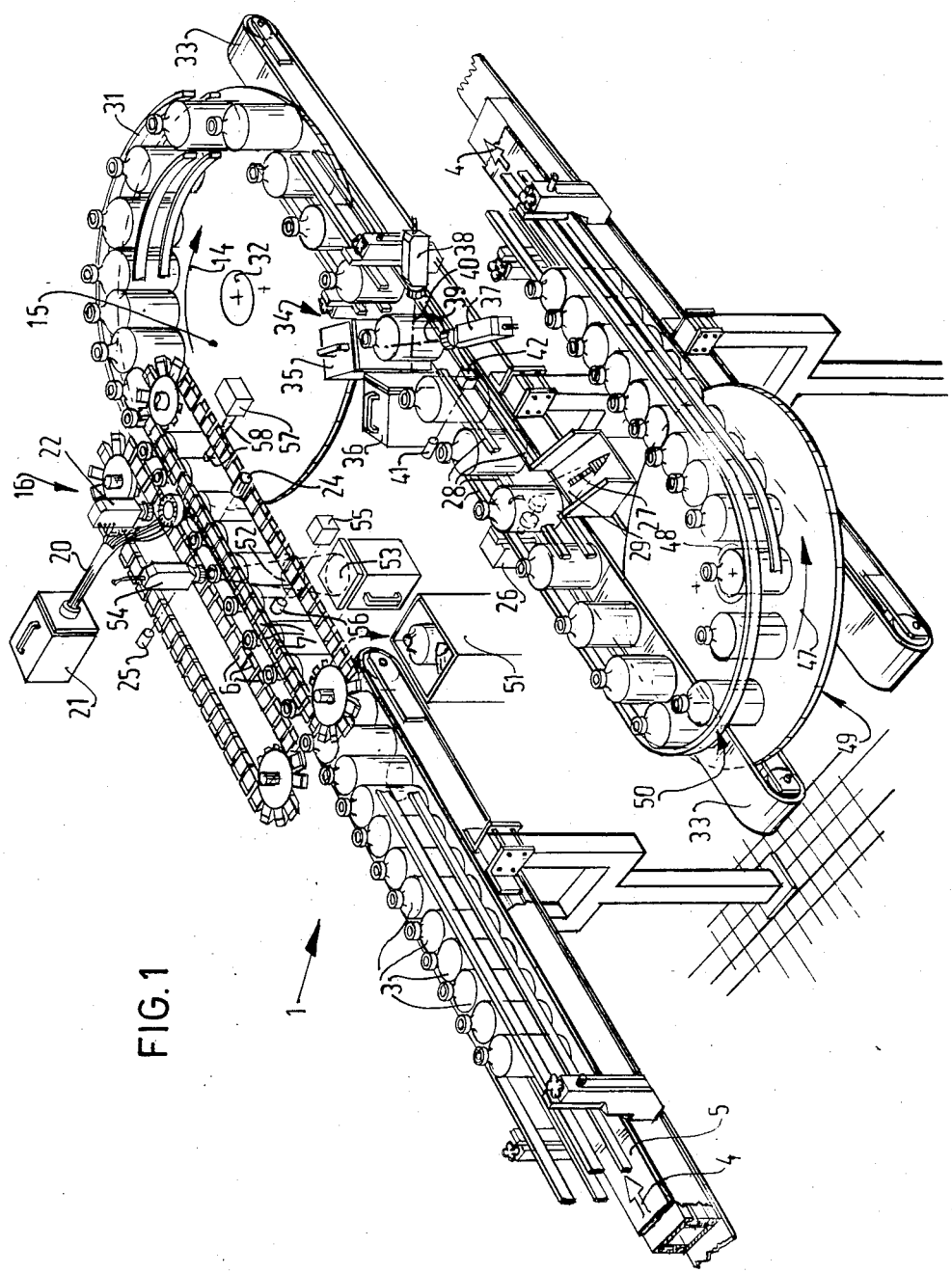

FIG. 1 shows a checking apparatus, generally referred to with reference number 1, for the determination of imperfections, e.g. in or at the wall, the bottom and also the sealing surfaces and at the inner and outer surfaces of glass bottles supplied by a supplying apparatus, e.g. a production apparatus by means of a transport appartus guiding the bottles 3 along a predetermined path. The transport direction of bottles 3 along said path is indicated with arrows 4.

After leaving the supply apparatus bottles 3 are further transported by a conveyor 5 supplying the bottles to a transport means consisting of two conveyors 6, 7, and shown in more detail in FIG. 3. Conveyors 6, 7 are chain conveyors, on the links 8 of which metal strips 9 are fixed, carrying more or less flexible fingers 10. As can be clearly seen in FIG. 3, the fingers 10 exhibit a somewhat tapering shape towards their free ends. Therewith a certain adaptation to the shape of the bottles 3 is obtained. The outer edges of fingers 10 support the collar 11 present on the neck 12 of each bottle 3.

The conveyor 5 is so long that a certain overlap with the conveyors 6, 7 is present, in such a way that a good take-over of the bottles 3 by the conveyors 6, 7 of the conveyor 5 is ensured. The height of the free edges of fingers 10 relative to the level of the conveyor 5 has, as will be clear, to be chosen in such a way that a good adaptation is obtained with the size of the bottles. In this respect it should be noted that also relatively small bottles have to be gripped surely. With the take-over of taller bottles during the take-over a somewhat larger height-difference has to be removed; by the flexibility of fingers 10 shock phenomena caused hereby are effectively eliminated.

At the end of the operative length of conveyors 6, 7 the transported bottles are taken over again by a spacing disc 15 to be described later and rotatably driven according to an arrow 14.

In the area of the operative part of conveyors 6, 7 a checking apparatus 52 is positioned for investigation of the bottoms and a checking apparatus 16 for the determination of imperfections at the collars of the bottles carried by conveyors 6, 7. The discussion of these apparatus 52 and 16 will follow now with reference to FIG. 3.

The checking apparatus 52 comprises a flash lamp 53 and a video camera 54 having a substantially vertical optical axis in common. A lamp 55 and a photocell 56 are positioned in such a way that the light beam emitted by lamp 55 in the direction of photocell 56 is interrupted by a passing bottle at the moment on which the bottle passes along the checking apparatus 52. The interruption of the light beam causes a changing in the output signal of photocell 56 causing the flash lamp 53 to be triggered, and supplying a flash at the correct moment.

The video camera 54 is positioned exactly above the neck of the passing bottles, and especially in such a position that it can see without obstacles the whole bottom to be checked of the passing bottles 3. As will be obvious, the flash lamp is positioned under the transparent bottom.

The bottles 3 carried by conveyors 6, 7 are guided below and along a circle 19 of light conductors 20, connected on a schematically indicated manner with a flash lamp 21. The axis of the ring 19 coincides with the optical axis of video camera 22. As indicated in FIG. 2 flash lamp 21 is coupled with a central control unit 23, an input of which is connected with a photo cell 24 cooperating with a lamp 25, said photo cell and said lamp being positioned in the way indicated in FIG. 1 in such a way, that on the passing of a bottle of the middle of the ring 19 a related signal is supplied by a photo cell 24 to the central control unit 23, said signal serving as triggering for the ignition of the flash lamp 21. Thus this lamp emits a flash at the moment on which a bottle 3 passes with the axis of its collar 11 the optical axis of camera 22, also the axis of ring 19.

The video camera 22 supplies a video-output signal to the central control unit 23. That unit 23 also comprises a reference, with which the input signal is compared in order to verify whether the upper edge of the related bottle contains imperfections. If this is the case, after a delay related with the transport speed of the bottles energization of a ejection means 26 takes place by which the related bottle is ejected at the place indicated in FIG. 1 in the direction of arrow 27.

A conveyor 13 guides the bottles 3 after leaving the spacing disc 15 within side guidings 28 exhibiting at the location of the ejection means 26 an interruption at one side corresponding with a not shown container or removal means for rejected bottles.

Side guidings 28 exhibit in the embodiment according to FIG. 1 a bend 31 and under that bend 31 the above mentioned, rotatably driven spacing disc 15, carrying the passing bottles 3 is present, the rotation axis 32 of which is relative to bend 31 positioned excentrically, in such a way that bottles 3 are accelerated in their paths in order to obtain a minimum free distance between succeeding bottles 3. From FIG. 1 it will be clear that the supply part of the side guidings 28 are radially positioned closer to the rotation axis 32 than the removal part thereof.

After having left the spacing disc 15 the bottles 3 are further transported by a further conveyor 33 transporting the bottles along a third checking apparatus 34. This checking apparatus 34 comprises two flash lamps 35, 36 and two video cameras 37, 38 cooperating therewith. The optical axes of the flash lamp 35 and video camera 37, and flash lamp 36 and video camera 38 respectively indicated by reference numbers 39, 40 respectively, cross in the middle longitudinal plane of the path of the bottles 3, said path been determined by the side guidings 28. Next to said path further a lamp 41 and a photo cell 42 cooperating therewith is positioned for supplying a trigger signal on the moment on which a bottle 3 passes with its longitudinal axis the crossing point or the crossing axis of the optical axes 39, 40. The video cameras 37, 38 supply their output signals to the central control unit 23, that compares the video output signals with a reference and energizes in case of detected imperfections in the related bottle the ejection means 26 that ejects a rejected bottle.

After having passed the ejection means 26 the transported bottles 3 are taken over by a despacing disc 49 rotatably driven around an axis 48 in the direction of arrow 47. The side guidings exhibit a second bend 50, below which the despacing disc 49 is positioned. The rotation axis 48 of disc 49 is placed excentrically with respect to the bend 50, in such a way that the bottles 3 are decelerated in their paths, causing their mutual distance to be decreased so that generally they will touch each other. It will be obvious that the supply part in the region of the second bend 50 of the side guidings 28 is radially positioned far away of the rotating axis 48 relatively to its discharge part.

Accepted bottles are further transported for storage, transportation, a filling operation or the like.

The apparatus 1 further gives an automatic discharge of bottles 3 that are not standing on the conveyor 5, but e.g. lying, toppled over, or bottles, the colour of which is not or partially not present. Such bottles namely cannot be gripped by the conveyors 6, 7, due to which at the end of the ooperative part of conveyor 5 they fall down into a container 51.

Beyond the second checking apparatus 16 a marking apparatus 57 is positioned. This apparatus is adapted for providing through a nozzle 58 a passing container, after it has been checked by the video camera 54 or 22 and found defective, with a spot of paint or ink. In relation with the known driving speed of the conveyors 6, 7 the moment, on which a container having passed the video cameras 54 and 22, respectively reaches the nozzle 58 can be assessed exactly.

Such a defective container, i.e. a container to be ejected, is further transported towards the third checking apparatus 34, that detects the spot of paint or ink present on the side wall of the related container and energizes on basis of that detection result the ejection means 26 for ejecting the relative container.

Figure 4:
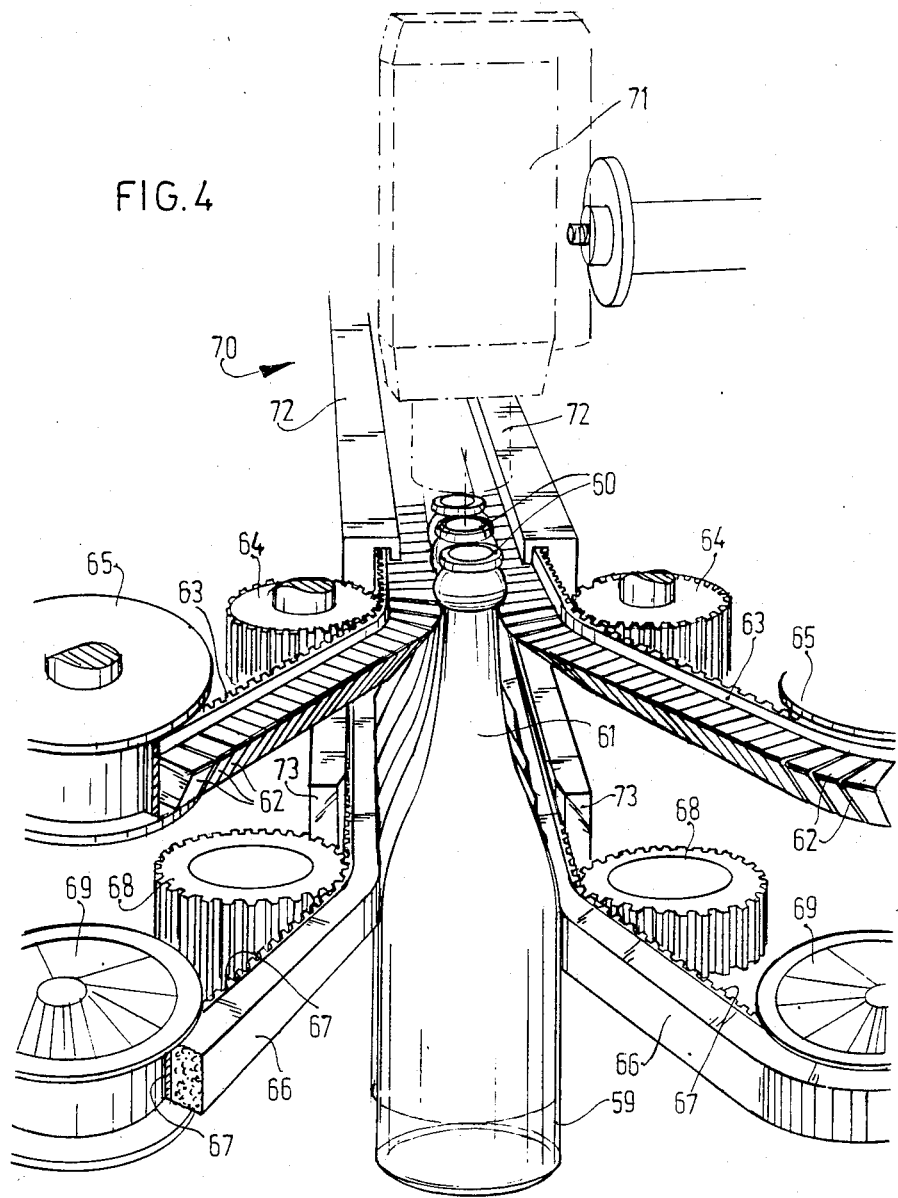

FIG. 4 shows the hanging transportation of bottles 59 in a rectilinear path, in a variant of the apparatus described hereinbefore. According to this variant, the bottles are hung by their collars 60 of their necks 61 between tapering, more or less resilient lips 62 fixed to corresponding toothed belts 63 made of synthetic resin. These toothed belts are driven with equal speeds by gear wheels 64 and guided by rollers 65.

In this embodiment the bottles 59 are with their sides also supported by resilient belts 66 running together therewith, said belts being provided on toothed belts 67 driven by gear wheels 68 and guided by rollers 69. Due to this embodiments the transportation of the bottles 69 takes place in a very reliable manner and with exclusion of slewing movements if any.

The toothed belts 63 are with their sides guided by guiding beams 72 having adapted internal profilation over the rectilinear part 70 of the path above which a video camera 71 is placed. For the adaptation to bottles having another neck diameter these guiding beams can be displaced towards and away from each other by means of not shown means. Muutatis mutandis the same is valid for guiding beams 73, serving for the side guiding of the toothed belts 67.

Lighting means for emitting light from the underside through the bottoms of the bottles 59, are not shown.

If desired the resilient belts 66 can at their surfaces directed to the bottles be provided with a covering layer having desired mechanical properties. In this case one can refer to a material having a desired friction coefficient in common with the bottles and/or a material prohibiting the formation of cracks in the belts 66.

We claim:

1. Apparatus for inspecting containers for defects, each container being of the type having a bottom and a neck presenting an open mouth and each defining an axis passing through its bottom and through its open mouth, which comprises the combination of transport means for traveling the containers along a predetermined path having a rectilinear portion, said transport means including, in said rectilinear portion of the path, means for suspending the containers from the necks thereof so that their axes travel along a line of the rectilinear path portion, sensing means for viewing along a vertical optical axis penetrating said rectilinear portion of the path and for generating a rejection signal in response to detection of each defective container, illuminating means for momentarily illuminating each container in coordinated relation to the passage of its axis relative to the position of said optical axis, and ejection means responsive to the rejection signals for ejecting the defective containers.

2. Apparatus as defined in claim 1 wherein said optical axis is in line with the path traveled by the axes of said containers.

3. Apparatus as defined in claim 2 wherein said illuminating means comprises mechanism overlying said rectilinear path portion for momentarily illuminating the mouth of each container as it passes thereunder.

4. Apparatus as defined in claim 2 wherein one of said illuminating means and said sensing means is located below said bottoms of the containers and the other is located above the open tops of the containers.

5. Apparatus as defined in claim 1 wherein said illuminating means comprises mechanism overlying said rectilinear path portion for momentarily illuminating the mouth of each container as it passes thereunder.

6. Apparatus as defined in claim 5 including second sensing means and second illuminating means operating in coordinated relation along said rectilinear portion of the path for viewing through the bottoms of the containers and for generating a rejection signal in response to detection of each defective container by the second sensing means.

7. Apparatus as defined in claim 1 wherein one of said illuminating means and said sensing means is located below said bottoms of the containers and the other is located above the open tops of the containers.

8. Apparatus for inspecting containers for defects, each container being of the type having a bottom and a neck presenting an open mouth and each defining an axis passing through its bottom and centrally through its open mouth, which comprises the combination of transport means for traveling the containers along a predetermined path having a rectilinear portion, said transport means including, in said rectilinear portion of the path, means for suspending the containers from the necks thereof so that their axes travel along a line of the rectilinear path portion and the mouths thereof are steadied by the means for suspending, sensing means for viewing along a vertical optical axis penetrating said rectilinear portion of the path and for generating a rejection signal in response to detection of each defective container, illuminating means for momentarily illuminating each container as its axis coincides with said optical axis, and ejection means responsive to the rejection signals for ejecting the defective containers.

9. Apparatus as defined in claim 8 wherein said optical axis is in line with the path traveled by the axes of said containers.

10. Apparatus as defined in claim 9 wherein one of said illuminating means and said sensing means is located below said bottoms of the containers and the other is located above the open tops of the containers.

11. Apparatus as defined in claim 8 wherein said illuminating means comprises mechanism overlying said rectilinear path portion for momentarily illuminating the mouth of each container as it passes thereunder.

12. Apparatus as defined in claim 11 including second sensing means and second illuminating means operating in coordinated relation along said rectilinear portion of the path for viewing through the bottoms of the containers and for generating a rejection signal in response to detection of each defective container by the second sensing means.

13. Apparatus as defined in claim 9 wherein said illuminating means comprises mechanism overlying said rectilinear path portion for momentarily illuminating the mouth of each container as it passes thereunder.

14. Apparatus as defined in claim 8 wherein one of said illuminating means and said sensing means is located below said bottoms of the containers and the other is located above the open tops of the containers.

* * * * *

UNITED STATES PATENT AND TRADEMARK OFFICE
CERTIFICATE OF CORRECTION

PATENT NO. : 4,680,463
DATED : July 14, 1987
INVENTOR(S) : Pieter H. Lutgendorf et al It is certified that error appears in the above-identified patent and that said Letters Patent is hereby corrected as shown below:

On the title page assignee should read

--(73) Assignees: Thomassen and Drijver-Verblifa N.V., The Netherlands and Hajime Industries Ltd., Tokyo, Japan, part interest --.

Signed and Sealed this

Twenty-second Day of December, 1987

Attest:

DONALD J. QUIGG

*Attesting Officer*    *Commissioner of Patents and Trademarks*